US012721558B2

(12) United States Patent
Vogtmeier et al.

(10) Patent No.: US 12,721,558 B2
(45) Date of Patent: Sep. 1, 2026

(54) MEDICAL IMAGE ACQUISITION UNIT ASSISTANCE APPARATUS

(71) Applicant: KONINKLIJKE PHILIPS N.V., Eindhoven (NL)

(72) Inventors: Gereon Vogtmeier, Aachen (DE); Mark Thomas Johnson, Arendonk (BE); Steffen Weiss, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/709,146

(22) PCT Filed: Oct. 5, 2023

(86) PCT No.: PCT/EP2023/077546
§ 371 (c)(1),
(2) Date: May 10, 2024

(87) PCT Pub. No.: WO2024/078956
PCT Pub. Date: Apr. 18, 2024

(65) Prior Publication Data

US 2025/0241570 A1 Jul. 31, 2025

(30) Foreign Application Priority Data

Oct. 10, 2022 (EP) .................................... 22200500

(51) Int. Cl.
*A61B 5/16* (2006.01)
*A61B 5/00* (2006.01)

(52) U.S. Cl.
CPC ............ *A61B 5/165* (2013.01); *A61B 5/0033* (2013.01); *A61B 5/163* (2017.08); *A61B 5/7405* (2013.01); *A61B 5/744* (2013.01)

(58) Field of Classification Search
CPC ........ G16H 50/20; A61B 5/163; A61B 5/165; A61B 5/744; A61B 5/002;
(Continued)

(56) References Cited

U.S. PATENT DOCUMENTS

2007/0225574 A1 9/2007 Ueda
2020/0268339 A1* 8/2020 Hao ...................... A61B 6/544
(Continued)

FOREIGN PATENT DOCUMENTS

EP 3673806 A2 7/2020
WO 2019/173237 A1 9/2019

OTHER PUBLICATIONS

International Search Report and Written Opinion Dated Jan. 3, 2024 for International Application No. PCT/EP2023/077546 Filed Oct. 5, 2023.

*Primary Examiner* — Gerald Johnson
(74) *Attorney, Agent, or Firm* — Larry Liberchuk

(57) ABSTRACT

The present invention relates to a medical image acquisition unit assistance apparatus (10), the apparatus comprising: —at least one sensor (20); and —a processing unit (30); wherein one or more sensors of the at least one sensor is configured to acquire sensor data of a person observing a patient undergoing a medical scan by a medical image acquisition unit; wherein the one or more sensors is configured to provide the acquired sensor data of the person observing the patient undergoing the medical scan to the processing unit; wherein the processing unit is configured to determine a state of the person observing the patient undergoing the medical scan comprising utilization of the acquired sensor data of the person observing the patient undergoing the medical scan; wherein the processing unit is configured to determine an overall state of the patient comprising utilization of the determined state of the person.

20 Claims, 2 Drawing Sheets

(58) Field of Classification Search
CPC .............. G06F 2203/011; G06V 40/15; G06V 40/174; G06V 40/20; A61M 2021/005
See application file for complete search history.

(56) References Cited

U.S. PATENT DOCUMENTS

| | | | | |
|---|---|---|---|---|
| 2020/0330055 | A1* | 10/2020 | Talgorn | A61B 6/461 |
| 2021/0259789 | A1* | 8/2021 | Wright | A61B 34/35 |
| 2021/0386489 | A1* | 12/2021 | Wright | A61B 90/37 |

* cited by examiner

FIG. 1
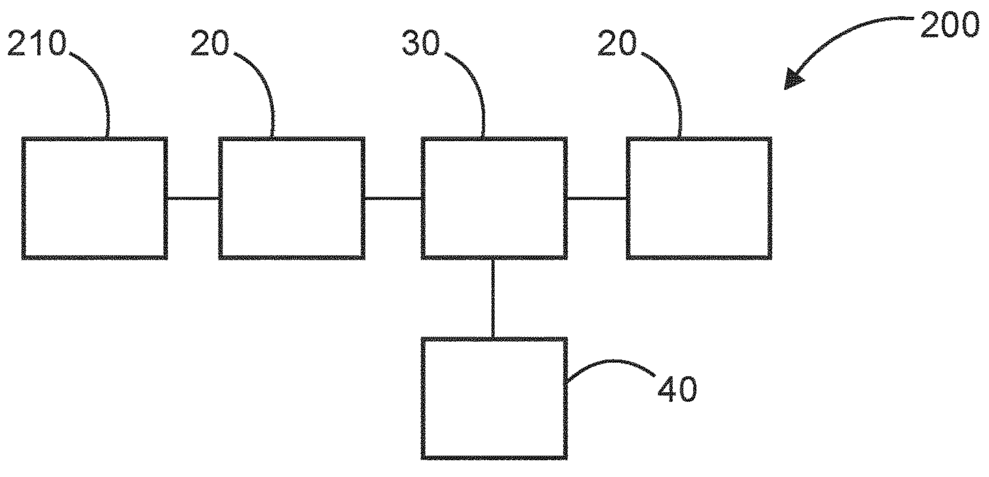
FIG. 2
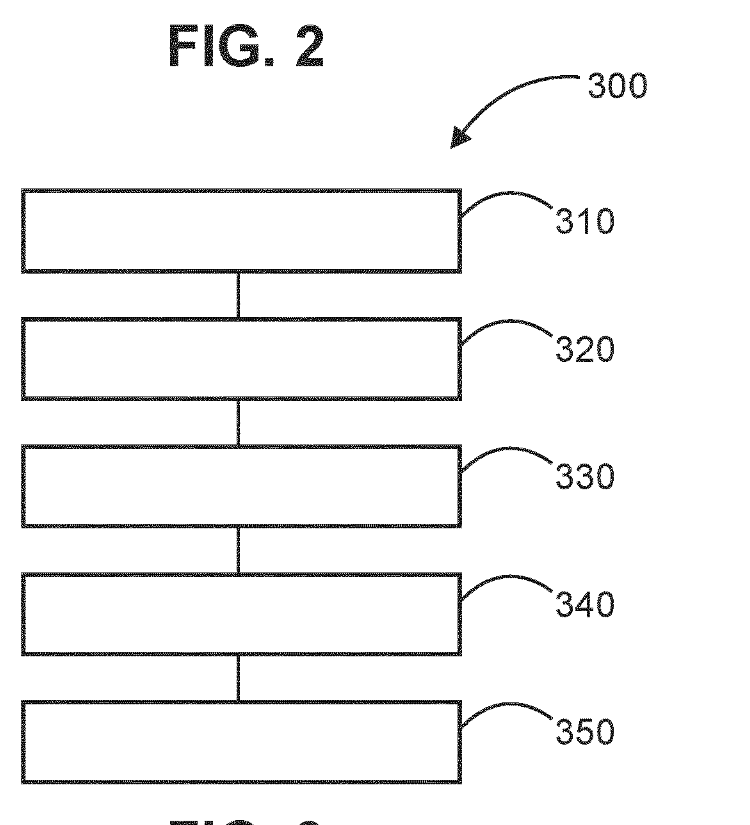
FIG. 3

MEDICAL IMAGE ACQUISITION UNIT ASSISTANCE APPARATUS

CROSS REFERENCE TO RELATED APPLICATIONS

This application is the U.S. National Phase application under 35 U.S.C. § 371 of International Application No. PCT/EP2023/077546 filed Oct. 5, 2023, which claims the benefit of European Patent Application Number 22200500.1 filed Oct. 10, 2022. These applications are hereby incorporated by reference herein.

FIELD OF THE INVENTION

The present invention relates to a medical image acquisition unit assistance apparatus, a medical image acquisition unit assistance system, a medical image acquisition unit assistance method, a computer program element, and a computer readable medium.

BACKGROUND OF THE INVENTION

For a diagnostic imaging scan with a medical image acquisition unit, such as an X-ray CT unit, an MRI unit, or other medical image acquisition units such as a PET unit, to achieve resultant images with the required quality it is essential that the patient follows the guidance procedure. To ensure this appropriate feedback needs to be provided to the patient in order that they can follow the guidance procedure, and do not deviate from the guidance procedure such as moving incorrectly, and if they do deviate from the guidance procedure that they can be brought back effectively to follow the guidance procedure. This not only achieves the required quality of the resultant images, but also ensure that the diagnostic imaging scan does not need to be terminated if the patient moves too much.

Deviation from the guidance procedure can be caused because patients can feel pain, misunderstand commands, not hear commands, become confused, become anxious, and even start to panic. However, it is extremely difficult to determine that the patient is feeling pain, has misunderstood a command, not heard the command, has become confused, has become anxious, and has started to panic in order to provide appropriate guidance and/or help to the patient in order that the patient can be brought back to following the guidance procedure.

There is a need to address these problems.

SUMMARY OF THE INVENTION

It would be advantageous to have an improved technique helping acquire medical image scans. The object of the present invention is solved with the subject matter of the independent claims, wherein further embodiments are incorporated in the dependent claims.

In a first aspect, there is provided a medical image acquisition unit assistance apparatus, the apparatus comprising:

at least one sensor; and a processing unit.

One or more sensors of the at least one sensor is configured to acquire sensor data of a person observing a patient undergoing a medical scan by a medical image acquisition unit. The one or more sensors is configured to provide the acquired sensor data of the person observing the patient undergoing the medical scan to the processing unit. The processing unit is configured to determine a state of the person observing the patient undergoing the medical scan comprising utilization of the acquired sensor data of the person observing the patient undergoing the medical scan. The processing unit is configured to determine an overall state of the patient comprising utilization of the determined state of the person.

In this manner, rather than determine a state of the patient directly from the patient another person who is observing the patient, who could be a trusted person to the patient such as a friend or relative, is monitored and from sensor data of that observing person a state of the patient can be determined.

To put this another way, the person observing the patient undergoing a medical scan is used as sensor and this person is monitored to determine objective data that can determine how that person is reacting to how anxious or relaxed the patient is, and this enables timely and appropriate feedback to be provided to the patient.

In an example, the one or more sensors comprises a camera configured to acquire imagery of the person observing the patient undergoing the medical scan. The camera is configured to provide the acquired imagery of the person observing the patient undergoing the medical scan to the processing unit. The determination of the state of the person an comprise utilization of the acquired imagery of the person observing the patient undergoing the medical scan.

In an example, the acquired imagery of the person observing the patient undergoing the medical scan comprises imagery of the person's face. The determination of the state of the person observing the patient undergoing the medical scan can comprise image analysis of the imagery of the person's face.

In an example, the acquired imagery of the person observing the patient undergoing the medical scan comprises imagery of the person's body. The determination of the state of the person observing the patient undergoing the medical scan can comprise image analysis of the imagery of the person's body.

In face recognition one can differentiate between a relaxed state and an "unnormal" state. Details are fast changes in the expression and also non natural face expressions.

Also or alternatively, one can determine if the person is becoming anxious from their body language, if they cross their arms, clasps their hands, lean forward, pulls there head to one side etc.

In an example, the one or more sensors comprises one or more vital sign sensors. The one or more vital sign sensors are configured to acquire vital sign sensor data of the person observing the patient undergoing the medical scan. The one or more vital sign sensors are configured to provide the acquired vital sign sensor data of the person observing the patient undergoing the medical scan to the processing unit. The determination of the state of the person observing the patient undergoing the medical scan can comprise utilization of the vital sign sensor data of the person.

In an example, the one or more sensors comprises a gaze direction sensor system. The gaze direction sensor system is configured to determine a gaze direction of the person observing the patient undergoing the medical scan. The gaze direction sensor system is configured to provide the determined gaze direction of the person observing the patient undergoing the medical scan to the processing unit. The determination of the state of the person observing the patient undergoing the medical scan can comprise utilization of the determined gaze direction of the person.

In this manner it can be determined where the person observing the patient is looking: are they generally looking around; are they concentrating on the patient's face; are they concentrating on the patient's hand that has just gripped the edge of the examination table; have they been generally looking around the patient and then suddenly focused exclusively on the patient's face? All of this information that can be part of determining the state of the person observing the patient can be utilized in determining an overall state of the patient.

This information can be used at the same time, through correlation, with a determined monitored state of the patient.

In an example, the at least one sensor comprises a second camera, and the second camera is configured to acquire imagery of the patient undergoing the medical scan.

In an example, the apparatus comprises a display unit. The display unit is configured to display the acquired imagery of the patient undergoing the medical scan. The display unit is configured to enable the person to observe the patient undergoing the medical scan.

In an example, the second camera is configured to provide the acquired imagery of the patient undergoing the medical scan to the processing unit. The processing unit is configured to determine a monitored state of the patient comprising utilization of the acquired imagery of the patient. The determination of the overall state of the patient can comprise utilization of the determined monitored state of the patient.

In an example, the acquired imagery of the patient undergoing the medical scan comprises imagery of the patient's face. The determination of the monitored state of the patient undergoing the medical scan can comprise image analysis of the imagery of the patient's face.

In an example, the acquired imagery of the patient undergoing the medical scan comprises imagery of the patients' body. The determination of the monitored state of the patient undergoing the medical scan can comprise image analysis of the imagery of the patient's body.

In face recognition one can differentiate between a relaxed state and an "unnormal" state. Details are fast changes in the expression and also non natural face expressions.

Also or alternatively, one can determine if the patient is becoming anxious from their body language, if they form their hands into fists, or grip the edge of the examination table or hand rail etc.

In an example, the at least one sensor comprises one or more second vital sign sensors. The one or more second vital sign sensors are configured to acquire vital sign sensor data of the patient undergoing the medical scan. The one or more second vital sign sensors are configured to provide the acquired vital sign sensor data of the patient undergoing the medical scan to the processing unit. The determination of the monitored state of the patient undergoing the medical scan can comprise utilization of the vital sign sensor data of the patient.

In an example, the determination of the overall state of the patient comprises utilization of a correlation between the determined state of the person observing the patient undergoing the medical scan and the determined monitored state of the patient undergoing the medical scan.

In this manner, the correlation can be utilized as a sensor data quality check and the level of importance.

In an example, the processing unit is configured to generate an avatar of the person observing the patient undergoing the medical scan. The feedback provided to the patient comprises utilization of the avatar presented on a display unit and/or played via a loudspeaker.

Thus, for example when the person observing the patient undergoing the medical scan is doing so remotely viewing the patient via video relay or is looking at the patient from a distance where the person cannot see the patient or where it is determined that the person observing the patient would not provide appropriate feedback (e.g. they are determined to be too anxious themselves) an avatar of the person observing the patient can be provided on a display screen to the patient to provide calming feedback to the patient and/or an avatar of the person observing the patient can be provided via a loudspeaker to the patient to provide calming feedback to the patient.

It is thus to be noted here that avatar can mean a synthetic visual presentation and/or a synthetic audio presentation.

In a second aspect, there is provided a medical image acquisition unit assistance system, the system comprising:

a medical image acquisition unit;

at least one sensor; and a processing unit.

One or more sensors of the at least one sensor is configured to acquire sensor data of a person observing a patient undergoing a medical scan by the medical image acquisition unit. The one or more sensors is configured to provide the acquired sensor data of the person observing the patient undergoing the medical scan to the processing unit. The processing unit is configured to determine a state of the person observing the patient undergoing the medical scan comprising utilization of the acquired sensor data of the person observing the patient undergoing the medical scan. The processing unit is configured to determine an overall state of the patient comprising utilization of the determined state of the person.

In a third aspect, there is provided a medical image acquisition unit assistance method, comprising:

acquiring by one or more sensors of the sensor data of a person observing a patient undergoing a medical scan by a medical image acquisition unit;

providing the acquired sensor data of the person observing the patient undergoing the medical scan to a processing unit;

determining by the processing unit a state of the person observing the patient undergoing the medical scan comprising utilizing the acquired sensor data of the person observing the patient undergoing the medical scan; and determining by the processing unit an overall state of the patient comprising utilizing the determined state of the person.

In an aspect, there is provided a computer program element for controlling an apparatus according to the first aspect which when executed by a processor is configured to carry out the method of the third aspect.

In an aspect, there is provided a computer program element for controlling a system according to the second aspect which when executed by a processor is configured to carry out the method of the third aspect.

Thus, according to aspects, there is provided computer program elements controlling one or more of the apparatuses/systems as previously described which, if the computer program element is executed by a processor, is adapted to perform the method as previously described.

According to another aspect, there is provided computer readable media having stored the computer elements as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawing:

FIG. 1 shows a schematic representation of an example of a medical image acquisition unit assistance apparatus;

FIG. 2 shows an example of a medical image acquisition unit assistance system;

FIG. 3 shows an example of a medical image acquisition unit assistance method.

DETAILED DESCRIPTION OF EMBODIMENTS

Figure 4:
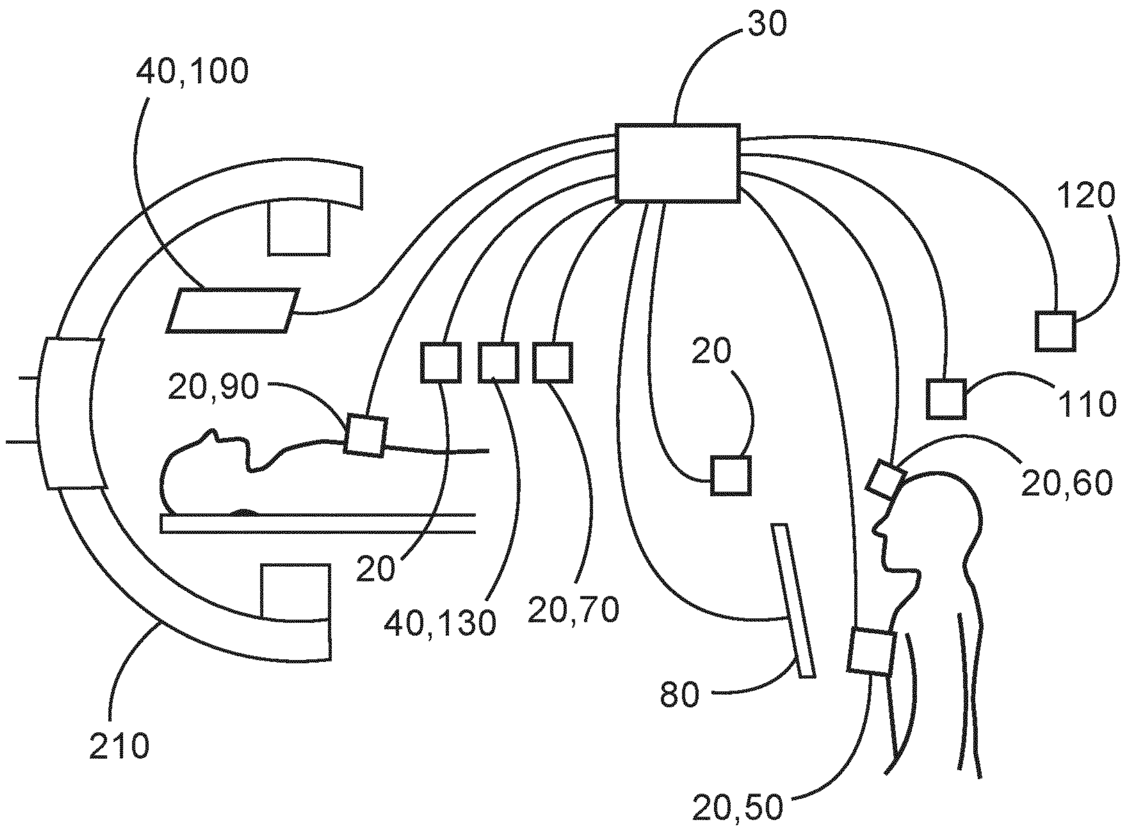
FIG. 4 shows an example of a detailed embodiment of a medical image acquisition unit assistance system.

FIG. 1 shows an example of a medical image acquisition unit assistance apparatus 10. The apparatus 10 comprises at least one sensor 20, and a processing unit 30. One or more sensors of the at least one sensor is configured to acquire sensor data of a person observing a patient undergoing a medical scan by a medical image acquisition unit. The one or more sensors is configured to provide the acquired sensor data of the person observing the patient undergoing the medical scan to the processing unit. The processing unit is configured to determine a state of the person observing the patient undergoing the medical scan comprising utilization of the acquired sensor data of the person observing the patient undergoing the medical scan. The processing unit is configured to determine an overall state of the patient comprising utilization of the determined state of the person.

In this manner, rather than determine a state of the patient directly from the patient another person who is observing the patient, who could be a trusted person to the patient such as a friend or relative, is monitored and from sensor data of that observing person a state of the patient can be determined.

To put this another way, the person observing the patient undergoing a medical scan is used as sensor and this person is monitored to determine objective data that can determine how that person is reacting to how anxious or relaxed the patient is, and this enables timely and appropriate feedback to be provided to the patient.

In an example, the processing unit is configured to determine an adapted mode of the operation of the medical image acquisition unit comprising utilization of the determined overall state of the patient.

In this manner, it can be determined to switch a scan to low noise or pause it when audio communication is happening or is about to be provided to the patient.

In an example, the apparatus comprises an output unit 40, and the output unit is configured to provide feedback to the patient comprising utilization of the determined overall state of the patient.

In an example, the person is observing the patient directly, being in the same room as the patient or viewing the patient through a window.

In an example, the person is observing the patient remotely, via video imagery of the patient being provided to the person.

In an example, the processing unit is configured to select one or more speech selections from a database based on the determined overall state of the patient, and wherein the feedback to the patient comprises audio play of the one or more speech selections.

In an example, the one or more speech selections were recorded by the person.

Thus, the person who is now observing the patient undergoing the scan can be provided with a series of different situations that arise with other patients and can record what they consider would be comforting words if it was the patient themselves in these situations.

In an example, the apparatus comprises a microphone 110 configured to acquire speech data from the person observing the patient undergoing the medical scan. The microphone is configured to provide the acquired speech data to the processing unit. The processing unit is configured to extract one or more segments of the speech data and/or generate new speech data comprising utilization of the determined overall state of the patient, and the feedback provided to the patient comprises the extracted one or more segments of the speech data and/or the generated new speech data.

In an example, the apparatus comprises a microphone 110 and a loud speaker 120. The processing unit is configured to play an audio message on the loud speaker, and the audio message is generated based on the determined state of the person observing the patient undergoing the medical scan. The microphone is configured to acquire speech data from the person in response to the playing of the audio message. The microphone is configured to provide the acquired speech data from the person to the processing unit, and the feedback to the patient comprises utilization of the acquired speech data.

In an example, the feedback to the patient comprises a repeat of a last instruction.

In an example, the feedback to the patient comprises an indication that the medical scanner is making a normal noise.

In an example, the feedback to the patient comprises an indication of how much longer an existing scan section will last.

In an example, the feedback to the patient comprises an indication of how long the next scan section will last.

In an example, the feedback to the patient comprises an indication of what is going to happen next.

Thus, if it is determined that the person observing the patient observing the patient undergoing a medical scan is becoming anxious, a question can be asked if they consider the patient to be becoming anxious. The person may then relay that the patient did not understand the last instruction relayed to them or is becoming nervous as the medical scanner goes through a particularly noisy part of a scan routine. The processing unit can then relay appropriate feedback to the patient, such as repeating the last instruction or indicating that the medical scanner is making a normal noise and explaining how much longer this part of the scan will take or indicate prior to scan sections what will happen next and for how long.

According to an example, the one or more sensors comprises a camera configured to acquire imagery of the person observing the patient undergoing the medical scan. The camera is configured to provide the acquired imagery of the person observing the patient undergoing the medical scan to the processing unit. The determination of the state of the person cam comprise utilization of the acquired imagery of the person observing the patient undergoing the medical scan.

According to an example, the acquired imagery of the person observing the patient undergoing the medical scan comprises imagery of the person's face, and the determination of the state of the person observing the patient undergoing the medical scan can comprise image analysis of the imagery of the person's face. Additionally or alternatively the acquired imagery of the person observing the patient undergoing the medical scan comprises imagery of the person's body, and the determination of the state of the person observing the patient undergoing the medical scan can comprise image analysis of the imagery of the person's body.

In face recognition one can differentiate between a relaxed state and an "unnormal" state. Details are fast changes in the expression and also non natural face expressions.

Also or alternatively, one can determine if the person is becoming anxious from their body language, if they cross their arms, clasps their hands, lean forward, pulls there head to one side etc.

According to an example, the one or more sensors comprises one or more vital sign sensors 50. The one or more vital sign sensors are configured to acquire vital sign sensor data of the person observing the patient undergoing the medical scan. The one or more vital sign sensors are configured to provide the acquired vital sign sensor data of the person observing the patient undergoing the medical scan to the processing unit. The determination of the state of the person observing the patient undergoing the medical scan can comprise utilization of the vital sign sensor data of the person.

In an example, the one or more sensors comprises a microphone, and the microphone is configured to acquire sound data from the person observing the patient undergoing the medical scan. The determination of the state of the person observing the patient undergoing the medical scan can comprise utilization of audio analysis of the sound data of the person.

Thus, in audio analysis you can detect if the person becomes nervous, anxious via changing the speed, frequency, homogeneity and interruption of the speaking.

In an example, the one or more sensors comprises one or more of: heart beat sensor, breath rate sensor, skin conductivity sensor.

Thus, the anxiety of the person observing the patient can be determined and indeed it can be determined if the person is starting to panic because they can see that the patient is starting to panic.

For example, the person observing the patient can start to become more active in speaking to the patient, and the processing unit can is necessary edit or block or create synthetic abridged versions of this speech that is actually provide to the patient, and at the same time the person's breathing rate and/or heart beat rate and/or degree of perspiration increases and this can be used to determine that the patient undergoing the medical scan is beginning to have a problem and appropriate feedback provided to the patient.

According to an example, the one or more sensors 20 comprises a gaze direction sensor system 60, and wherein the gaze direction sensor system is configured to determine a gaze direction of the person observing the patient undergoing the medical scan. The gaze direction sensor system is configured to provide the determined gaze direction of the person observing the patient undergoing the medical scan to the processing unit. The determination of the state of the person observing the patient undergoing the medical scan can comprise utilization of the determined gaze direction of the person.

In this manner it can be determined where the person observing the patient is looking: are they generally looking around; are they concentrating on the patient's face; are they concentrating on the patient's hand that has just gripped the edge of the examination table; have they been generally looking around the patient and then suddenly focused exclusively on the patient's face? All of this information that can be part of determining the state of the person observing the patient can be utilized in determining an overall state of the patient.

This information can be used at the same time, through correlation, with a determined monitored state of the patient.

According to an example, the at least one sensor comprises a second camera 70, and the second camera is configured to acquire imagery of the patient undergoing the medical scan.

According to an example, the apparatus comprises a display unit 80, and the display unit is configured to display the acquired imagery of the patient undergoing the medical scan. The display unit is configured to enable the person to observe the patient undergoing the medical scan.

According to an example, the second camera is configured to provide the acquired imagery of the patient undergoing the medical scan to the processing unit, and the processing unit is configured to determine a monitored state of the patient comprising utilization of the acquired imagery of the patient. The determination of the overall state of the patient can comprise utilization of the determined monitored state of the patient.

According to an example, the acquired imagery of the patient undergoing the medical scan comprises imagery of the patient's face, and the determination of the monitored state of the patient undergoing the medical scan can comprise image analysis of the imagery of the patient's face. Additionally or alternatively the acquired imagery of the patient undergoing the medical scan comprises imagery of the patients' body, and the determination of the monitored state of the patient undergoing the medical scan can comprise image analysis of the imagery of the patient's body.

In face recognition one can differentiate between a relaxed state and an "unnormal" state. Details are fast changes in the expression and also non natural face expressions.

Also or alternatively, one can determine if the patient is becoming anxious from their body language, if they form their hands into fists, or grip the edge of the examination table or hand rail etc.

According to an example, the at least one sensor comprises one or more second vital sign sensors 90, and the one or more second vital sign sensors are configured to acquire vital sign sensor data of the patient undergoing the medical scan. The one or more second vital sign sensors are configured to provide the acquired vital sign sensor data of the patient undergoing the medical scan to the processing unit. The determination of the monitored state of the patient undergoing the medical scan can comprise utilization of the vital sign sensor data of the patient.

According to an example, the determination of the overall state of the patient comprises utilization of a correlation between the determined state of the person observing the patient undergoing the medical scan and the determined monitored state of the patient undergoing the medical scan.

In this manner, the correlation can be utilized as a sensor data quality check and the level of importance.

For example, if the patient shows no signs of anxiety from the determined monitored state of the patient but the person observing the patient shows signs of anxiety, it could be that the patient is indeed not anxious or showing very subtle signs of anxiety that only a person who knows the patient can detect. Thus, the person observing the patient can be asked if everything appears to be ok with the patient, and this information can be used to feedback to the patient, where for example a synthesized voice feedback can be provided to the patient rather than provide the patient with voice data from the anxious person that could be negative. In other words, the processing unit can block voice feedback from the person observing the patient when appropriate.

However, if patient is determined to be anxious but the person observing the patient is not anxious, but showed particular interest in the patient, such as generally looking at all of the patient but then focusing on the patient's face as the anxiety of the patient increases it can be determined that the patient is indeed anxious and direct feedback from this calm person to the patient can be particular useful to the patient.

Also, if both the patient and the person observing the patient are determined to be anxious, it can be determined that the patient really is anxious and appropriate feedback provided to the patient.

A decision tree system can have the different feedback actions defined with respect to the monitored state of the patient and the state of the person as part of the overall state of the patient.

According to an example, the processing unit is configured to generate an avatar of the person observing the patient undergoing the medical scan, and the feedback provided to the patient comprises utilization of the avatar presented on a display unit 100 and/or played via a loudspeaker 130.

Thus, for example when the person observing the patient undergoing the medical scan is doing so remotely viewing the patient via video relay or is looking at the patient from a distance where the patient cannot see the patient or where it is determined that the person observing the patient would not provide appropriate feedback (e.g. they are determined to be too anxious themselves) an avatar of the person observing the patient can be provided on a display screen to the patient to provide calming feedback to the patient and/or an avatar of the person observing the patient can be provided via a loudspeaker to the patient to provide calming feedback to the patient.

It is thus to be noted here that avatar can mean a synthetic visual presentation and/or a synthetic audio presentation.

In an example, the generation of the avatar comprises a selection of an avatar stream from a plurality of avatar streams saved on a database based on the determined overall state of the patient.

In an example, the plurality of avatar streams were created on the basis of a plurality of video recordings of the person and/or audio recordings of the person.

Thus, the person who is now observing the patient undergoing the scan can be provided with a series of different situations that arise with other patients, and a recording can be made of how they would feedback to "their" patient is these situations, and avatar streams can be created for these situations and the processing unit selects the most appropriate avatar stream to present/play to the patient.

In an example, sensor data of the person can be acquired whilst they are presented with these different situations.

FIG. 2 shows an example of a medical image acquisition unit assistance system 200. The system comprises a medical image acquisition unit 210, at least one sensor 20, and a processing unit 30. One or more sensors of the at least one sensor is configured to acquire sensor data of a person observing a patient undergoing a medical scan by the medical image acquisition unit. The one or more sensors is configured to provide the acquired sensor data of the person observing the patient undergoing the medical scan to the processing unit. The processing unit is configured to determine a state of the person observing the patient undergoing the medical scan comprising utilization of the acquired sensor data of the person observing the patient undergoing the medical scan. The processing unit is configured to determine an overall state of the patient comprising utilization of the determined state of the person.

In an example, the processing unit is configured to determine an adapted mode of the operation of the medical image acquisition unit comprising utilization of the determined overall state of the patient.

In an example, the system comprises an output unit 40, and the output unit is configured to provide feedback to the patient comprising utilization of the determined overall state of the patient.

In an example, the person is observing the patient directly, being in the same room as the patient or viewing the patient through a window.

In an example, the person is observing the patient remotely, via video imagery of the patient being provided to the person.

In an example, the processing unit is configured to select one or more speech selections from a database based on the determined overall state of the patient, and wherein the feedback to the patient comprises audio play of the one or more speech selections.

In an example, the one or more speech selections were recorded by the person.

In an example, the system comprises a microphone 110 configured to acquire speech data from the person observing the patient undergoing the medical scan. The microphone is configured to provide the acquired speech data to the processing unit. The processing unit is configured to extract one or more segments of the speech data and/or generate new speech data comprising utilization of the determined overall state of the patient. The feedback provided to the patient can comprise the extracted one or more segments of the speech data and/or the generated new speech data.

In an example, the system comprises a microphone 110 and a loud speaker 120, and the processing unit is configured to play an audio message on the loud speaker. The audio message is generated based on the determined state of the person observing the patient undergoing the medical scan. The microphone is configured to acquire speech data from the person in response to the playing of the audio message. The microphone is configured to provide the acquired speech data from the person to the processing unit, and the feedback to the patient can comprise utilization of the acquired speech data.

In an example, the feedback to the patient comprises a repeat of a last instruction.

In an example, the feedback to the patient comprises an indication that the medical scanner is making a normal noise.

In an example, the feedback to the patient comprises an indication of how much longer an existing scan section will last.

In an example, the feedback to the patient comprises an indication of how long the next scan section will last.

In an example, the feedback to the patient comprises an indication of what is going to happen next.

In an example, the one or more sensors comprises a camera configured to acquire imagery of the person observing the patient undergoing the medical scan. The camera is configured to provide the acquired imagery of the person observing the patient undergoing the medical scan to the processing unit. The determination of the state of the person comprises utilization of the acquired imagery of the person observing the patient undergoing the medical scan.

In an example, the acquired imagery of the person observing the patient undergoing the medical scan comprises imagery of the person's face, and the determination of the state of the person observing the patient undergoing the medical scan can comprise image analysis of the imagery of the person's face.

In an example, the acquired imagery of the person observing the patient undergoing the medical scan comprises imagery of the person's body, and the determination of the state of the person observing the patient undergoing the medical scan can comprise image analysis of the imagery of the person's body.

In an example, the one or more sensors comprises one or more vital sign sensors 50. The one or more vital sign sensors are configured to acquire vital sign sensor data of the person observing the patient undergoing the medical scan. The one or more vital sign sensors are configured to provide the acquired vital sign sensor data of the person observing the patient undergoing the medical scan to the processing unit. The determination of the state of the person observing the patient undergoing the medical scan can comprise utilization of the vital sign sensor data of the person.

In an example, the one or more sensors comprises a microphone, and the microphone is configured to acquire sound data from the person observing the patient undergoing the medical scan. The determination of the state of the person observing the patient undergoing the medical scan comprises utilization of audio analysis of the sound data of the person.

In an example, the one or more sensors comprises one or more of: heart beat sensor, breath rate sensor, skin conductivity sensor.

In an example, the one or more sensors comprises a gaze direction sensor system 60, and the gaze direction sensor system is configured to determine a gaze direction of the person observing the patient undergoing the medical scan. The gaze direction sensor system is configured to provide the determined gaze direction of the person observing the patient undergoing the medical scan to the processing unit. The determination of the state of the person observing the patient undergoing the medical scan can comprise utilization of the determined gaze direction of the person.

In an example, the at least one sensor comprises a second camera 70, and the second camera is configured to acquire imagery of the patient undergoing the medical scan.

In an example, the system comprises a display unit 80. The display unit is configured to display the acquired imagery of the patient undergoing the medical scan, and the display unit is configured to enable the person to observe the patient undergoing the medical scan.

In an example, the second camera is configured to provide the acquired imagery of the patient undergoing the medical scan to the processing unit. The processing unit is configured to determine a monitored state of the patient comprising utilization of the acquired imagery of the patient. The determination of the overall state of the patient can comprise utilization of the determined monitored state of the patient.

In an example, the acquired imagery of the patient undergoing the medical scan comprises imagery of the patient's face, and the determination of the monitored state of the patient undergoing the medical scan can comprise image analysis of the imagery of the patient's face.

In an example, the acquired imagery of the patient undergoing the medical scan comprises imagery of the patients' body, and the determination of the monitored state of the patient undergoing the medical scan can comprise image analysis of the imagery of the patient's body.

In an example, the at least one sensor comprises one or more second vital sign sensors 90, and the one or more second vital sign sensors are configured to acquire vital sign sensor data of the patient undergoing the medical scan. The one or more second vital sign sensors are configured to provide the acquired vital sign sensor data of the patient undergoing the medical scan to the processing unit. The determination of the monitored state of the patient undergoing the medical scan can comprise utilization of the vital sign sensor data of the patient.

In an example, the determination of the overall state of the patient comprises utilization of a correlation between the determined state of the person observing the patient undergoing the medical scan and the determined monitored state of the patient undergoing the medical scan.

In an example, the processing unit is configured to generate an avatar of the person observing the patient undergoing the medical scan, and the feedback provided to the patient comprises utilization of the avatar presented on a display unit 100 and/or played via a loudspeaker 130.

In an example, the generation of the avatar comprises a selection of an avatar stream from a plurality of avatar streams saved on a database based on the determined overall state of the patient.

In an example, the plurality of avatar streams were created on the basis of a plurality of video recordings of the person and/or audio recordings of the person.

In an example, sensor data of the person can be acquired whilst they are presented with these different situations.

FIG. 3 shows a medical image acquisition unit assistance method 300. The basic steps of the method 300 comprises:

- acquiring 310 by one or more sensors of the sensor data of a person observing a patient undergoing a medical scan by a medical image acquisition unit;
- providing 320 the acquired sensor data of the person observing the patient undergoing the medical scan to a processing unit;
- determining 330 by the processing unit a state of the person observing the patient undergoing the medical scan comprising utilizing the acquired sensor data of the person observing the patient undergoing the medical scan; and
- determining 340 by the processing unit an overall state of the patient comprising utilizing the determined state of the person.

In an example, the method comprises adapting by the processing unit a mode of the operation of the medical image acquisition unit comprising utilizing the determined overall state of the patient.

In an example, the method comprises outputting 350 by an output unit feedback to the patient comprising utilization of the determined overall state of the patient.

In an example, the person is observing the patient directly, being in the same room as the patient or viewing the patient through a window.

In an example, the person is observing the patient remotely, via video imagery of the patient being provided to the person.

In an example, the method comprises selecting by the processing unit one or more speech selections from a database based on the determined overall state of the patient, and wherein the feedback to the patient comprises audio play of the one or more speech selections.

In an example, the one or more speech selections were recorded by the person.

In an example, the method comprises acquiring by a microphone speech data from the person observing the patient undergoing the medical scan, and providing the acquired speech data to the processing unit, and extracting by the processing unit one or more segments of the speech data and/or generating by the processing unit new speech data comprising utilizing the determined overall state of the patient, and wherein the feedback provided to the patient comprises the extracted one or more segments of the speech data and/or the generated new speech data.

In an example, the method comprises playing an audio message on a loud speaker, wherein the audio message is generated based on the determined state of the person observing the patient undergoing the medical scan, and acquiring by a microphone speech data from the person in response to the playing of the audio message, and providing the acquired speech data from the person to the processing unit, and wherein the feedback to the patient comprises utilizing the acquired speech data.

In an example, the feedback to the patient comprises a repeat of a last instruction.

In an example, the feedback to the patient comprises an indication that the medical scanner is making a normal noise.

In an example, the feedback to the patient comprises an indication of how much longer an existing scan section will last.

In an example, the feedback to the patient comprises an indication of how long the next scan section will last.

In an example, the feedback to the patient comprises an indication of what is going to happen next.

In an example, the method comprises acquiring by a camera imagery of the person observing the patient undergoing the medical scan and providing the acquired imagery of the person observing the patient undergoing the medical scan to the processing unit, and the determining of the state of the person comprises utilizing the acquired imagery of the person observing the patient undergoing the medical scan.

In an example, the acquired imagery of the person observing the patient undergoing the medical scan comprises imagery of the person's face, and wherein the determining the state of the person observing the patient undergoing the medical scan comprises image analysing the imagery of the person's face; and/or wherein the acquired imagery of the person observing the patient undergoing the medical scan comprises imagery of the person's body, and wherein the determining the state of the person observing the patient undergoing the medical scan comprises image analysing the imagery of the person's body.

In an example, the method comprises acquiring by one or more vital sign sensors vital sign sensor data of the person observing the patient undergoing the medical scan and providing the acquired vital sign sensor data of the person observing the patient undergoing the medical scan to the processing unit, and wherein the determining the state of the person observing the patient undergoing the medical scan comprises utilizing the vital sign sensor data of the person.

In an example, the method comprises acquiring by a microphone sound data from the person observing the patient undergoing the medical scan, and wherein the determining the state of the person observing the patient undergoing the medical scan comprises utilizing audio analysis of the sound data of the person.

In an example, the one or more vital signs sensors comprises one or more of: heart beat sensor, breath rate sensor, skin conductivity sensor.

In an example, the method comprises determining by a gaze direction sensor system a gaze direction of the person observing the patient undergoing the medical scan and providing the determined gaze direction of the person observing the patient undergoing the medical scan to the processing unit, and wherein the determining the state of the person observing the patient undergoing the medical scan comprises utilizing the determined gaze direction of the person.

In an example, the method comprises acquiring by a second camera imagery of the patient undergoing the medical scan.

In an example, the method comprises displaying on a display unit the acquired imagery of the patient undergoing the medical scan, and wherein the display unit is configured to enable the person to observe the patient undergoing the medical scan.

In an example, the method comprises providing the acquired imagery of the patient undergoing the medical scan to the processing unit, and determining by the processing unit a monitored state of the patient comprising utilizing the acquired imagery of the patient, and wherein determining the overall state of the patient comprises utilizing the determined monitored state of the patient.

In an example, the acquired imagery of the patient undergoing the medical scan comprises imagery of the patient's face, and wherein the determining the monitored state of the patient undergoing the medical scan comprises image analysis of the imagery of the patient's face; and/or wherein the acquired imagery of the patient undergoing the medical scan comprises imagery of the patients' body, and wherein the determining the monitored state of the patient undergoing the medical scan comprises image analysis of the imagery of the patient's body.

In an example, the method comprises acquiring by one or more second vital sign sensors vital sign sensor data of the patient undergoing the medical scan and providing the acquired vital sign sensor data of the patient undergoing the medical scan to the processing unit, and wherein the determining the monitored state of the patient undergoing the medical scan comprises utilizing the vital sign sensor data of the patient.

In an example, the determining the overall state of the patient comprises utilizing a correlation between the determined state of the person observing the patient undergoing the medical scan and the determined monitored state of the patient undergoing the medical scan.

In an example, the method comprises generating by the processing unit an avatar of the person observing the patient undergoing the medical scan, and wherein the feedback provided to the patient comprises utilizing the avatar presented on a display unit and/or played via a loudspeaker 130.

In an example, the generating the avatar comprises selecting an avatar stream from a plurality of avatar streams saved on a database based on the determined overall state of the patient.

In an example, the plurality of avatar streams were created on the basis of a plurality of video recordings of the person and/or audio recordings of the person.

In an example, sensor data of the person can be acquired whilst they are presented with these different situations.

The medical image acquisition unit assistance apparatus, the medical image acquisition unit assistance system, the medical image acquisition unit assistance method are now described in further detail, where reference in again made to FIG. 4.

It was realised that by the inventors that feedback from family members or other trusted persons in direct communication with the patient helpful to provide guidance to the patient in a clear manner that the patient can follow and helps to create a good atmosphere, because the patient will listen in more detail and will follow the guidance of the family member or other trusted person. However, the inventors also realized that the family member or trusted person, who knows the patient very well, is able to recognize special situations for the patient, such as when the patient is feeling pain, when there have misunderstood a command, not heard a command, are beginning to feel anxious, and indeed starting to panic, and can pick up on these states of the patient much earlier than sensors sensing the patient. The inventors also established that the state of the family member or other trusted person changes as they observe these changes in the patient, such as the patient is feeling pain, they have misunderstood a command or not heard a command, are beginning to feel anxious or starting to panic. The inventors realized that these changes of state of the person observing the patient can be monitored to determine an objective state of the person observing the patient, and that this then can be used to determine a state of the patient. The inventors also established that the state of the person observing the patient can be easier to monitor than the state of the patient, in that the signs exhibited by the person, monitored by appropriate sensors, can be greater than the signs exhibited by the patient as monitored by appropriate sensors. Thus, the inventors realized that the person (family member or other trusted person) observing a patient undergo a medical scan can used in effect as an incredibly sensitive sensor to sense the state of the patient, and this state of the patient can be determined by monitoring the person observing the patient rather than monitoring the patient. However, the inventors established that by also monitoring the patient the accuracy of the determined state of the patient can be improved. This is now discussed in further detail below.

Below, the person observing the patient undergo the medical scan by a medical image acquisition unit (X-ray CT, MRI, PET etc.) who can be a family member or other trusted person is referred to below as a trusted person.

The trusted person can be in the examination room, where the medical image acquisition unit 210 is located, cannot always be present close to the patient, therefore technical means are used to establish a high quality audio/video connection from a room close to the imaging room or even from remote locations. This is provided by having a camera 70 that captures imagery of the patient, including that of the patient's face. A display unit 80 then presents this video imagery to the trusted person.

A microphone 110 is used to capture what the trusted person says, and a loud speaker 120 (such as in headphones) is used to relay information to the trusted person, such as asking what is happening with respect to the patient-determined from a change in state of the trusted person. The processing unit 30 can then process what the trusted person says and provide all of this speech directly to the patient if it will be helpful, relayed to the patient via an output unit 40 in the form of a loud speaker 130, that could be a set of headphones. However, the processing unit can extract out speech that is determined would not be helpful to the patient, and indeed generate a synthesized version of the trusted person's feedback if necessary—for example if the trusted person themselves is becoming anxious and directly relaying the speech of the anxious trusted person to the patient could be counter-productive, but the essence of what is being said would be helpful.

Thus, in effect the processing unit 30 provides for the detection and judgement of the feedback from the trusted person that acts as a sensitive observer. For a beneficial usage of the information sometimes the sensed reaction can however only go to the medical staff (for immediate action) without giving negative feedback to the patient (to make the patient more nervous in case something unnormal has been detected). Then as discussed above in essence "controlled or selected" feedback is given to the patient to have positive impact for the patient and the procedure.

Regarding the feedback provided to the patient via one or more feedback units 40, this can be via a display unit 100, that projects an avatar of the trusted person to the patient, providing audio and visual feedback to the patient. The avatar can be however just be a synthetic voice based avatar with no imagery, provided to the patient via a loudspeaker. The avatar can be generated by identifying potential situations, prior to the patient undergoing the scan, with appropriate messages that would be relayed to the patient, and related wording for guiding commands, explaining words or gestures to support the messaging. This can be done in a synthesis process that is done prior to the scan and an analyzed simulated scan sequence. Potential situations with attention points or guiding requests can be identified from the simulated sequence of the imaging scan. The use of a personal avatar is useful in the situation where the trusted person can become very nervous when observing the patient, and their actual real-time feedback would be counter-productive, or when the trusted person cannot provide real-time feedback.

Thus, several embodiments of the new apparatus, system and method involve a selection of the following: involvement of the trusted person in a local and/or remote connection; objectively monitoring the response(s) of the trusted person; objectively monitoring the response(s) of the trusted person; a decision system which determines what feedback from the trusted person is to be used and how it is to be used; training/preparation of the trusted person to know about the imaging procedure and the attention points where guidance and/or sensitive observation of the patient would be required; simulation of the procedure based on the scan parameters and the patient data; creation of an audio/video avatar.

It is to be noted, that whilst the new apparatus, system and method is described in terms of a trusted person supporting a patient during an imaging procedure, the embodiments described are not exclusively useful in the case of an imaging procedure but may also be applicable for other healthcare related procedures such as other diagnostic procedures, such as physical and psychological examinations, interventional procedures, therapy or Coaching procedures.

The following embodiments described how the new apparatus, system and method can be implemented.

Embodiment 1: Objective Measurement of Trusted Person

In this embodiment a system is provided that uses the measured response of the trusted person to assist in establishing the state of the patient undergoing the imaging procedure.

As described elsewhere, the trusted person is able to at least observe the patient. This can include:

The trusted person being physically present in the imaging room

The trusted person being in virtual contact with the patient, for example using an audio, video, VR or AR system In this development, only the trusted person is monitored by sensors 20 in order to assess their objective state. Example of such measurements include:

Vital signs (Heart rate (variations), breathing, skin conduction . . . ) using vital signs sensors 20, 50;

Panic detection (upcoming-early detection), using vital signs sensors 20, 50;

Voice analysis, acquired by a microphone 110 in the vicinity of the trusted persons;

Facial expressions, using a camera 20 observing the trusted person.

A standard camera can be used to monitor the trusted person, and vital signs sensing can be achieved via patches, smart watches etc.

Furthermore, the trusted person can be monitored to determine that the trusted person is actually paying attention to the patient, for example by monitoring that the gaze direction of the trusted person is directed towards the patient in the imaging area and more preferably at the face of the patient, using a gaze direction determination system 60.

An elevated response of the trusted person can be used to initiate a query to the trusted person, for example as to why they may becoming anxious, through utilization of a loudspeaker 120 near to the trusted person, that could be part of headphones, or via a message relayed by a display unit 80.

In particular, the response of the trusted person may be synchronised to a specific event during imaging, for example:

Moving the patient onto/off the bed;

Moving the patient into/out of the scanner;

Steps in the scanning sequence, particularly those associated with high noise levels;

Instructions delivered to the patient (breath hold, reposition);

Movement of staff members into the scanning area.

Embodiment 2: Objective Measurement of Trusted Person and Objective Measurement Patient In this embodiment a system is provided that uses the measured response of the trusted person and that of the patient themselves to assist in establishing the state of the patient undergoing the imaging procedure.

As described elsewhere, the trusted person is able to at least observe the patient. This could include:

The trusted person being physically present in the imaging room;

The trusted person being in virtual contact with the patient, for example using an audio, video, VR or AR system.

In this development, both the trusted person and patient are monitored in order to assess their objective states. Example of such measurements again include:

Vital signs (Heart rate (variations), breathing, skin conduction . . . ) using vital signs sensors 20, 50;

Panic detection (upcoming-early detection), using vital signs sensors 20, 50;

Voice analysis, acquired by a microphone 110 in the vicinity of the trusted persons;

Facial expressions, using a camera 20 observing the trusted person.

A standard camera can be used to monitor the trusted person, and vital signs sensing can be achieved via patches, smart watches etc.

Furthermore, the trusted person can be monitored to determine that the trusted person is actually paying attention to the patient, for example by monitoring that the gaze direction of the trusted person is directed towards the patient in the imaging area and more preferably at the face of the patient, using a gaze direction determination system 60.

In this embodiment, particular attention is paid to synchronous changes in the state of both the patient and the trusted person. The response of the trusted person is here used to improve the specificity of the monitoring the state of the patient: notably if both patient and trusted person become anxious at the same moment then there is a very high probability that the patient is indeed experiencing discomfort.

For example, a synchronous elevation of the response of both the trusted person and the patient is used to initiate a query to the trusted person, patient or both as to why they may becoming anxious. A query can be provided to the trusted person through utilization of a loudspeaker 120 near to the trusted person, that could be part of headphones, or via a message relayed by a display unit 80. A query can be provided to the patient through utilization of a loudspeaker 130 near to the patient, that could be part of headphones, or via a message relayed by a display unit 100.

Embodiment 3: Specific Feedback from the Trusted Person to the Patient

In certain situations, it is preferable not to directly feedback what the trusted person is saying to the patient, if for example the trusted person is themselves becoming very anxious and their voice and/or what they are saying indicates that this is happening, because the patient receiving this direct feedback could then become more anxious. Also, in some situations the trusted person may not be able to provide direct feedback to the patient.

Thus, at one level a data interface is provided that on the basis of the sensor data of the trusted person enables the system to utilize a function that filters and selects the communications from the trusted person and determine what information is sent to patient and what is sent to staff. The system can synthesize what the trusted person has said in order to provide feedback to the patient that provides helpful guidance, without the voice imparting any anxiety itself.

Also, the trusted person can be presented with a whole series of patient specific simulations of the procedure, along with analysis of all patient supporting activities along the scan like breathing performance (faster, slower, calm down, . . . ), moving/non-moving periods as well as all risk situations when guidance would be necessary (don't worry, that's normal, just few more seconds, it's ready soon). The trusted person can then be monitored as well, providing for a selection procedure for a trusted person. Features to be sensed/detected by the trusted person and the reaction includes: comfort, anxiety, stress, unnormal breathing, panic (upcoming-early detection), voice analysis, facial expressions, vital signs.

This enables audio simulation to be provided to the patient via a loudspeaker and/or an avatar to be generated that can be presented to the patient via a display unit 100 in order to provide appropriate guidance to the patient. An audio/video link can use the following technologies (emulation of virtual presence), NLP, deep voice, and the avatar creation could use methods from deep fake technologies.

In another exemplary embodiment, a computer program or computer program element is provided that is characterized by being configured to execute the method steps of any of the methods according to one of the preceding embodiments, on an appropriate apparatus or system.

The computer program element might therefore be stored on a computer unit, which might also be part of an embodiment. This computing unit may be configured to perform or induce performing of the steps of the method described above. Moreover, it may be configured to operate the components of the above described system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word “comprising” does not exclude other elements or steps, and the indefinite article “a” or “an” does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical image acquisition unit assistance apparatus, the apparatus comprising:

at least one sensor; and a processor;

wherein one or more sensors of the at least one sensor is configured to acquire sensor data of a person observing a patient undergoing a medical scan by a medical image acquisition unit;

wherein the one or more sensors is configured to provide the acquired sensor data of the person observing the patient undergoing the medical scan to the processor;

wherein the processor is configured to determine a state of the person observing the patient by using the acquired sensor data of the person observing the patient undergoing the medical scan; and wherein the processor is configured to determine an overall state of the patient by using the determined state of the person observing the patient.

2. The apparatus according to claim 1, wherein the one or more sensors comprises a camera configured to acquire imagery of the person observing the patient undergoing the medical scan, wherein the camera is configured to provide the acquired imagery of the person observing the patient undergoing the medical scan to the processor, wherein the state of the person observing the patient is determined by using the acquired imagery of the person observing the patient undergoing the medical scan.

3. The apparatus according to claim 2, wherein the acquired imagery of the person observing the patient undergoing the medical scan comprises imagery of the person’s face, and wherein the state of the person observing the patient is determined by analyzing the imagery of the person’s face; and/or wherein the acquired imagery of the person observing the patient undergoing the medical scan comprises imagery of the person’s body, and wherein the state of the person observing the patient is determined by analyzing the imagery of the person’s body.

4. The apparatus according to claim 1, wherein the one or more sensors comprises one or more vital sign sensors configured to acquire vital sign sensor data of the person observing the patient undergoing the medical scan, wherein the one or more vital sign sensors are configured to provide the acquired vital sign sensor data of the person observing the patient undergoing the medical scan to the processor, and wherein the state of the person observing the patient undergoing the medical scan is determined by using the vital sign sensor data of the person.

5. The apparatus according to claim 1, wherein the one or more sensors comprises a gaze direction sensor system configured to determine a gaze direction of the person observing the patient—undergoing the medical scan, wherein the gaze direction sensor system is configured to provide the determined gaze direction of the person observing the patient undergoing the medical scan to the processor, and wherein the state of the person observing the patient undergoing the medical scan is determined by using the determined gaze direction of the person.

6. The apparatus according to claim 1, wherein the at least one sensor comprises a second camera configured to acquire imagery of the patient undergoing the medical scan.

7. The apparatus according to claim 6, wherein the apparatus comprises a display configured to display the acquired imagery of the patient undergoing the medical scan, and wherein the display is configured to enable the person to observe the patient undergoing the medical scan.

8. The apparatus according to claim 6, wherein the second camera is configured to provide the acquired imagery of the patient undergoing the medical scan to the processor, wherein the processor is configured to determine a monitored state of the patient by using acquired imagery of the patient, and wherein the overall state of the patient is determined by using the determined monitored state of the patient.

9. The apparatus according to claim 8, wherein the acquired imagery of the patient undergoing the medical scan comprises imagery of the patient's face, and wherein the monitored state of the patient undergoing the medical scan comprises image analysis of the imagery of the patient's face; and/or wherein the acquired imagery of the patient undergoing the medical scan comprises imagery of the patients' body, and wherein the monitored state of the patient undergoing the medical scan is determined by analyzing the imagery of the patient's body.

10. The apparatus according to claim 1, wherein the at least one sensor comprises one or more second vital sign sensors, and wherein the one or more second vital sign sensors are configured to acquire vital sign sensor data of the patient undergoing the medical scan, wherein the one or more second vital sign sensors are configured to provide the acquired vital sign sensor data of the patient undergoing the medical scan to the processor, and wherein the monitored state of the patient undergoing the medical scan is determined by using the vital sign sensor data of the patient.

11. The apparatus according to claim 8, wherein the overall state of the patient is determined by using a correlation between the determined state of the person observing the patient undergoing the medical scan and the determined monitored state of the patient undergoing the medical scan.

12. The apparatus according to claim 1, wherein the processor is configured to generate an avatar of the person observing the patient undergoing the medical scan, and to utilize the avatar presented on a display and/or played via a loudspeaker.

13. A medical image acquisition unit assistance system, the system comprising:

a medical image acquisition unit assistance apparatus as claimed in claim 1.

14. A medical image acquisition unit assistance method, comprising:

acquiring by one or more sensors of the sensor data of a person observing a patient undergoing a medical scan by a medical image acquisition unit;

providing the acquired sensor data of the person observing the patient undergoing the medical scan to a processor;

determining by the processor a state of the person observing the patient undergoing the medical scan by using the acquired sensor data of the person observing the patient undergoing the medical scan; and determining by the processor an overall state of the patient by using the determined state of the person observing the patient.

15. A computer program element for controlling an apparatus according to claim 1.

16. The method according to claim 14, wherein the one or more sensors comprises a camera configured to acquire imagery of the person observing the patient undergoing the medical scan, wherein the camera is configured to provide acquired imagery of the person observing the patient undergoing the medical scan to the processor, wherein the state of the person is determined by using the acquired imagery of the person observing the patient undergoing the medical scan.

17. The method according to claim 16, wherein the acquired imagery of the person observing the patient undergoing the medical scan comprises imagery of the person's face, and wherein the state of the person observing the patient undergoing the medical scan is determined by analyzing the imagery of the person's face; and/or wherein the acquired imagery of the person observing the patient undergoing the medical scan comprises imagery of the person's body.

18. The method according to claim 17, wherein the determining of the state of the person observing the patient undergoing the medical scan further comprises image analysis of the imagery of the person's body.

19. The method according to claim 14, wherein the one or more sensors comprises one or more vital sign sensors, and wherein the one or more vital sign sensors are configured to acquire vital sign sensor data of the person observing the patient undergoing the medical scan, wherein the one or more vital sign sensors are configured to provide the acquired vital sign sensor data of the person observing the patient undergoing the medical scan to the processor, and wherein the state of the person observing the patient undergoing the medical scan is determined by using the vital sign sensor data of the person.

20. The method according to claim 14, wherein the one or more sensors comprises a gaze direction sensor system configured to determine a gaze direction of the person observing the patient undergoing the medical scan, wherein the gaze direction sensor system is configured to provide the determined gaze direction of the person observing the patient undergoing the medical scan to the processor, and wherein the state of the person observing the patient undergoing the medical scan is determined by using the determined gaze direction of the person.

* * * * *